(12) United States Patent
Sukovic et al.

(10) Patent No.: US 7,556,428 B2
(45) Date of Patent: Jul. 7, 2009

(54) SURGICAL NAVIGATION SYSTEM INCLUDING PATIENT TRACKER WITH REMOVABLE REGISTRATION APPENDAGE

(75) Inventors: Predrag Sukovic, Birmingham, MI (US); Miodrag Rakic, Redondo Beach, CA (US); James A. Bertolina, Portage, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 0 days.

(21) Appl. No.: 11/735,661

(22) Filed: Apr. 16, 2007

(65) Prior Publication Data

US 2007/0253541 A1 Nov. 1, 2007

Related U.S. Application Data

(60) Provisional application No. 60/791,983, filed on Apr. 14, 2006.

(51) Int. Cl.
*A61B 6/08* (2006.01)
(52) U.S. Cl. ........................................ 378/205; 378/20
(58) Field of Classification Search ......... 378/205–206, 378/163, 4–20
See application file for complete search history.

(56) References Cited

U.S. PATENT DOCUMENTS

| 4,341,220 | A | | 7/1982 | Perry |
| 5,588,430 | A | | 12/1996 | Bova et al. |
| 5,748,696 | A | * | 5/1998 | Fujita et al. ................... 378/4 |
| 5,954,647 | A | | 9/1999 | Bova et al. |
| 6,246,900 | B1 | * | 6/2001 | Cosman et al. ............. 600/426 |
| 6,741,883 | B2 | | 5/2004 | Gildenberg |
| 6,892,090 | B2 | | 5/2005 | Verard et al. |
| 6,932,823 | B2 | | 8/2005 | Grimm et al. |
| 7,024,237 | B1 | | 4/2006 | Bova et al. |
| 7,139,418 | B2 | | 11/2006 | Abovitz et al. |
| 2003/0179856 | A1 | * | 9/2003 | Mitschke et al. ............ 378/205 |
| 2004/0097952 | A1 | | 5/2004 | Sarin et al. |
| 2007/0038059 | A1 | | 2/2007 | Sheffer et al. |

\* cited by examiner

*Primary Examiner*—Hoon Song
(74) *Attorney, Agent, or Firm*—Carlson, Gaskey & Olds (57) ABSTRACT

A surgical navigation system includes a CT scanner that takes a plurality of x-ray images of a patient. A patient tracker including locators is attached to the patient, and a registration appendage is removably secured to the patient tracker in a known position and orientation. The registration appendage includes radio-opaque markers arranged in a predetermined geometric pattern. The registration appendage is viewable in a CT scan in situations where the locators of the patient tracker are outside of a field of view of the CT scanner.

46 Claims, 7 Drawing Sheets

SURGICAL NAVIGATION SYSTEM INCLUDING PATIENT TRACKER WITH REMOVABLE REGISTRATION APPENDAGE

REFERENCE TO RELATED APPLICATIONS

This application claims priority to U.S. Provisional Patent Application No. 60/791,983 filed on Apr. 14, 2006.

BACKGROUND OF THE INVENTION

The present invention relates generally to a surgical navigation system including a registration appendage removably attached to a patient tracker.

A surgical navigation system includes a CT scanner and a tracking system that tracks locators. A patient tracker can be attached to the patient to track the location of the patient. An additional structure including markers can be attached to the patient tracker. In prior surgical navigation systems, the additional structure is located on a side of the patient tracker that is away from a body of the patient, and therefore the markers may not be visible in a three dimensional CT image taken by the CT scanner.

SUMMARY OF THE INVENTION

A surgical navigation system includes a CT scanner that takes a plurality of x-ray images of a patient. The surgical navigation system also includes a patient tracker positioned on the patient having locators. A tracking system tracks the positions and orientations of the locators. A registration appendage including radio-opaque markers arranged in a predetermined geometric pattern is attached to the patient tracker in a known position and orientation. When the locators of the patient tracker are positioned outside of the field of view of the CT scanner, the registration appendage can be secured to the patient tracker. In one example, the patient tracker is positioned on a forehead of the patient, and the registration appendage is located between the patient tracker and a body of the patient.

When the CT scanner takes a CT scan of the patient, the radio-opaque markers of the registration appendage are located within the field of view of the CT scanner and appear in a three-dimensional CT image, allowing repeatable registration of the three-dimensional CT image relative to previous three-dimensional CT images. If an x-ray source of the CT scanner is collimated to scan a volume of interest of the patient, the radio-opaque markers are visible in a collimated three-dimensional CT image, allowing the images from the collimated CT scan to be registered relative to a previous CT scan.

DETAILED DESCRIPTION OF A PREFERRED EMBODIMENT

Figure 1:
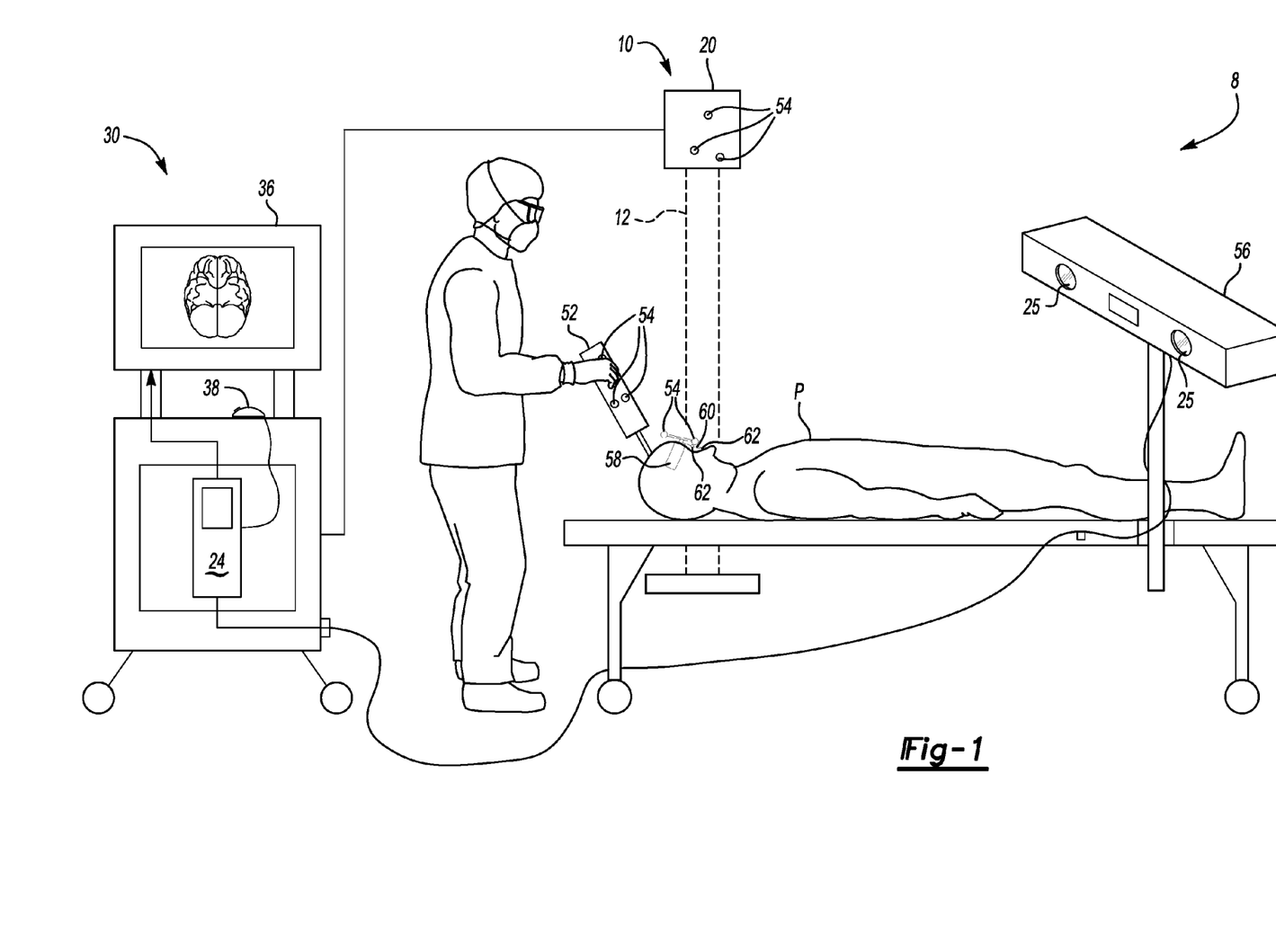
FIG. 1 illustrates a surgical navigation system.

FIG. 1 illustrates a surgical navigation system 8 including a CT scanner 10. Suitable CT scanners 10 are known.

Figure 2:
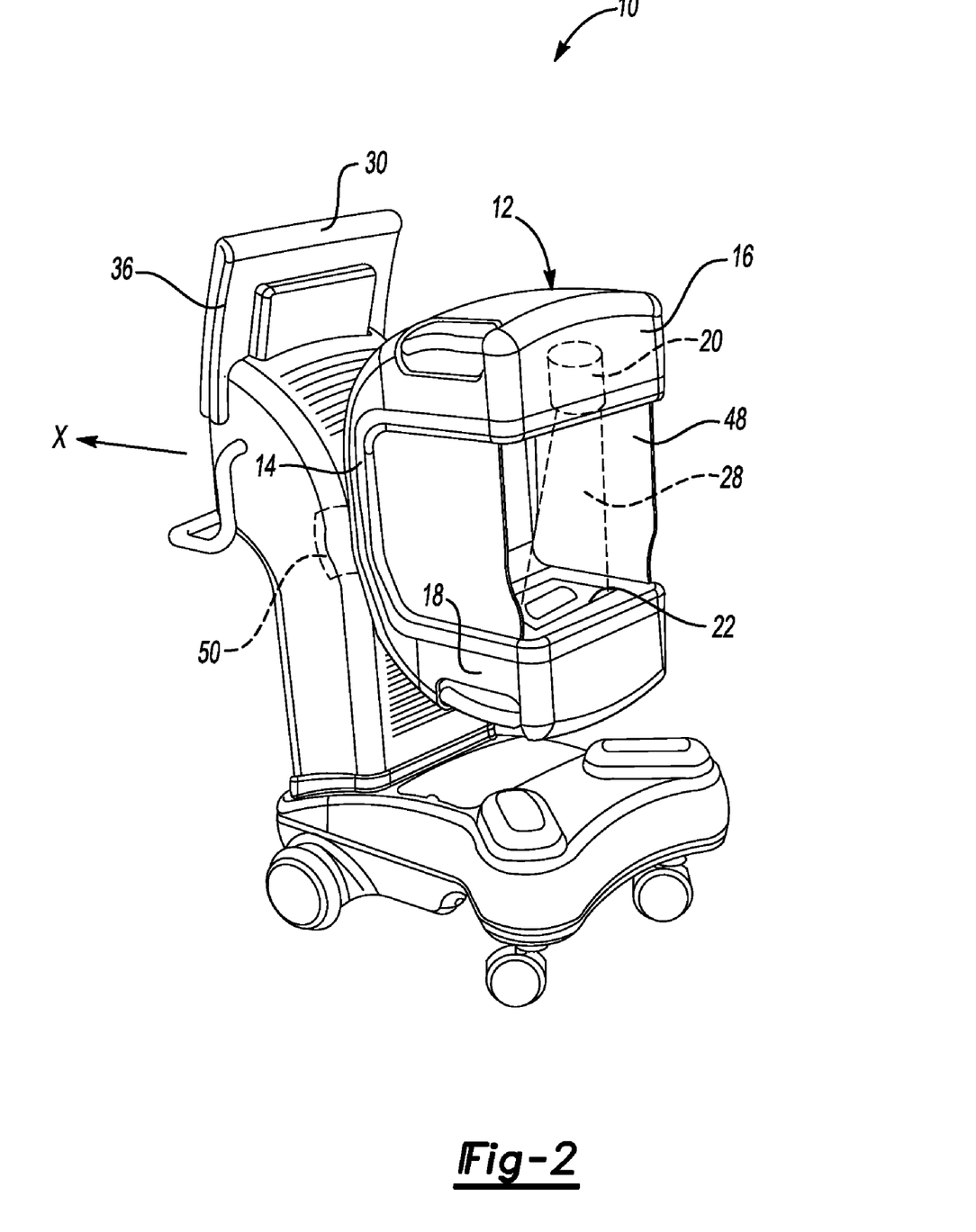
FIG. 2 illustrates a CT scanner of the surgical navigation system.

FIG. 2 illustrates one example CT scanner 10 used with the surgical navigation system 8. The CT scanner 10 includes an x-ray source 20 and an x-ray detector 22 spaced apart by a gantry 12 which is mounted to rotate at least partially about the patient P while taking a plurality of x-ray images of the patient P at a plurality of angularly spaced positions. The gantry 12 supports and houses components of the CT scanner 10. In one example, the gantry 12 includes a cross-bar section 14, and a first arm 16 and a second arm 18 each extend substantially perpendicularly from opposing ends of the cross-bar section 14 to form the c-shaped gantry 12. The first arm 16 houses the x-ray source 20 that generate x-rays 28. In one example, the x-ray source 20 is a cone-beam x-ray source. The second arm 18 houses a complementary flat-panel detector 22 spaced apart from the x-ray source 20. The x-rays 28 are directed toward the detector 22 which includes a converter (not shown) that converts the x-rays 28 from the x-ray source 20 to visible light and an array of photodetectors behind the converter to create an image. As the gantry 12 rotates about the patient P, the detector 22 takes a plurality of x-ray images at a plurality of rotational positions. Various configurations and types of x-ray sources 20 and detectors 22 can be utilized, and the invention is largely independent of the specific technology used for the CT scanner 10.

Figure 3:
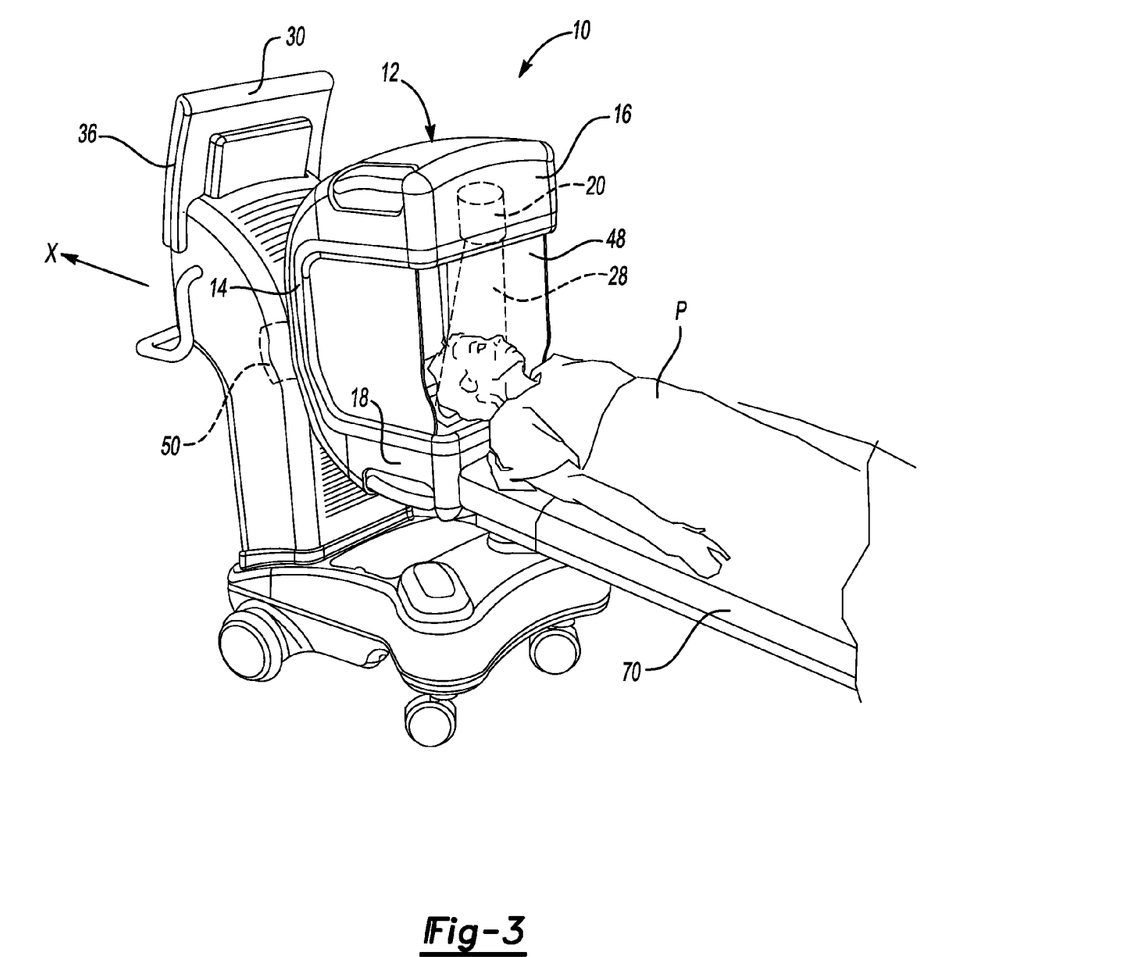
FIG. 3 illustrates the CT scanner with a part of a patient received in the CT scanner.

FIG. 3 illustrates the CT scanner 10 with a part of the patient P received in a space 48 between the first arm 16 and the second arm 18. A motor 50 rotates the gantry 12 about an axis of rotation X to obtain a plurality of x-ray images of the patient P at the plurality of rotational positions. The axis of rotation X is substantially centered within the gantry 12 and positioned between the x-ray source 20 and the detector 22. The gantry 12 can be rotated approximately slightly more than 360 degrees about the axis of rotation X. In one example, as shown in FIGS. 1 and 2, the axis of rotation X is substantially horizontal. In this example, the patient P is typically lying down on a table 70.

Figure 4:
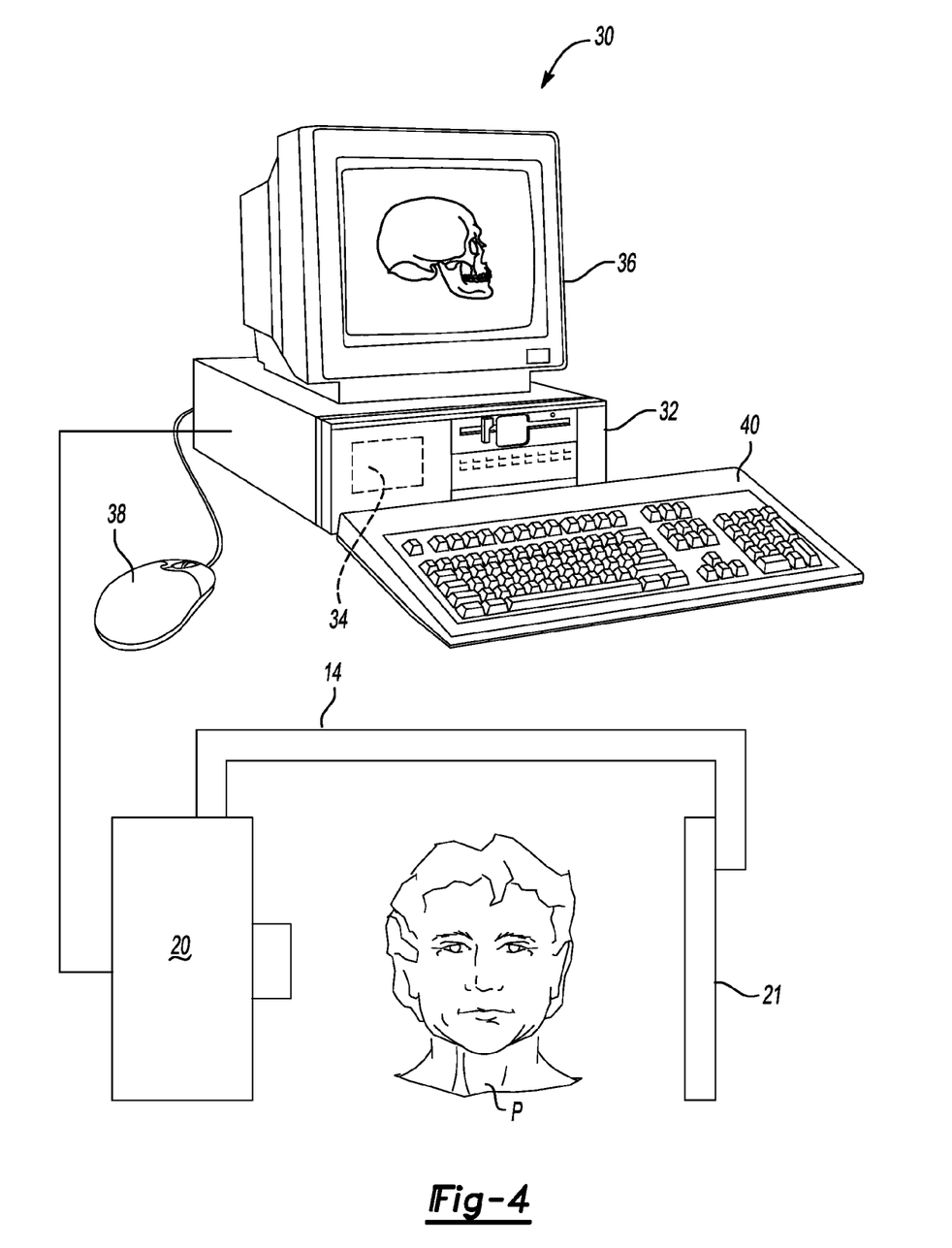
FIG. 4 illustrates a computer employed with the surgical navigation system.

As shown schematically in FIG. 4, the CT scanner 10 further includes a computer 30 having a microprocessor or CPU 32, a storage 34 (memory, hard drive, optical, and/or magnetic, etc), a display 36, a mouse 38, a keyboard 40 and other hardware and software for performing the functions described herein. The computer 30 powers and controls the x-ray source 20 and the motor 50. The plurality of x-ray images taken by the detector 22 are sent to the computer 30. The computer 30 generates a three-dimensional CT image from the plurality of x-ray images utilizing any known techniques and algorithms. The three-dimensional CT image is stored on the storage 34 of the computer 30 and can be displayed on the display 36 for viewing.

Returning to FIG. 1, the surgical navigation system 8 includes at least one surgical instrument 52 having fiducials or locators 54. The surgical navigation system 8 also includes a patient tracker 58 having a plurality of locators 54 mounted in a fixed, known arrangement. The patient tracker 58 is either secured in a fixed position to the patient P or removably secured to the patient P in a repeatable manner (such that the locations of the locators 54 relative to the patient P are constant). Optionally, a plurality of locators 54 may also be fixed to the CT scanner 10 (on the x-ray source 20, the detector 22 or the gantry 12) such that the location of the CT scanner 10 relative to a tracking system 56 is known.

The tracking system 56 tracks the position of the locators 54 and locates the position and optionally, the orientation, of each of the locators 54 via RF, electromagnetic, optical or other signals. The locators 54 may be passive or active, such as simple reflectors or transmitters or some combination. The tracking system 56 includes sensors 25 which may be CCDs that optically detect the locators 54 or RF receivers that receive wireless signals from the locators 54.

Figure 5:
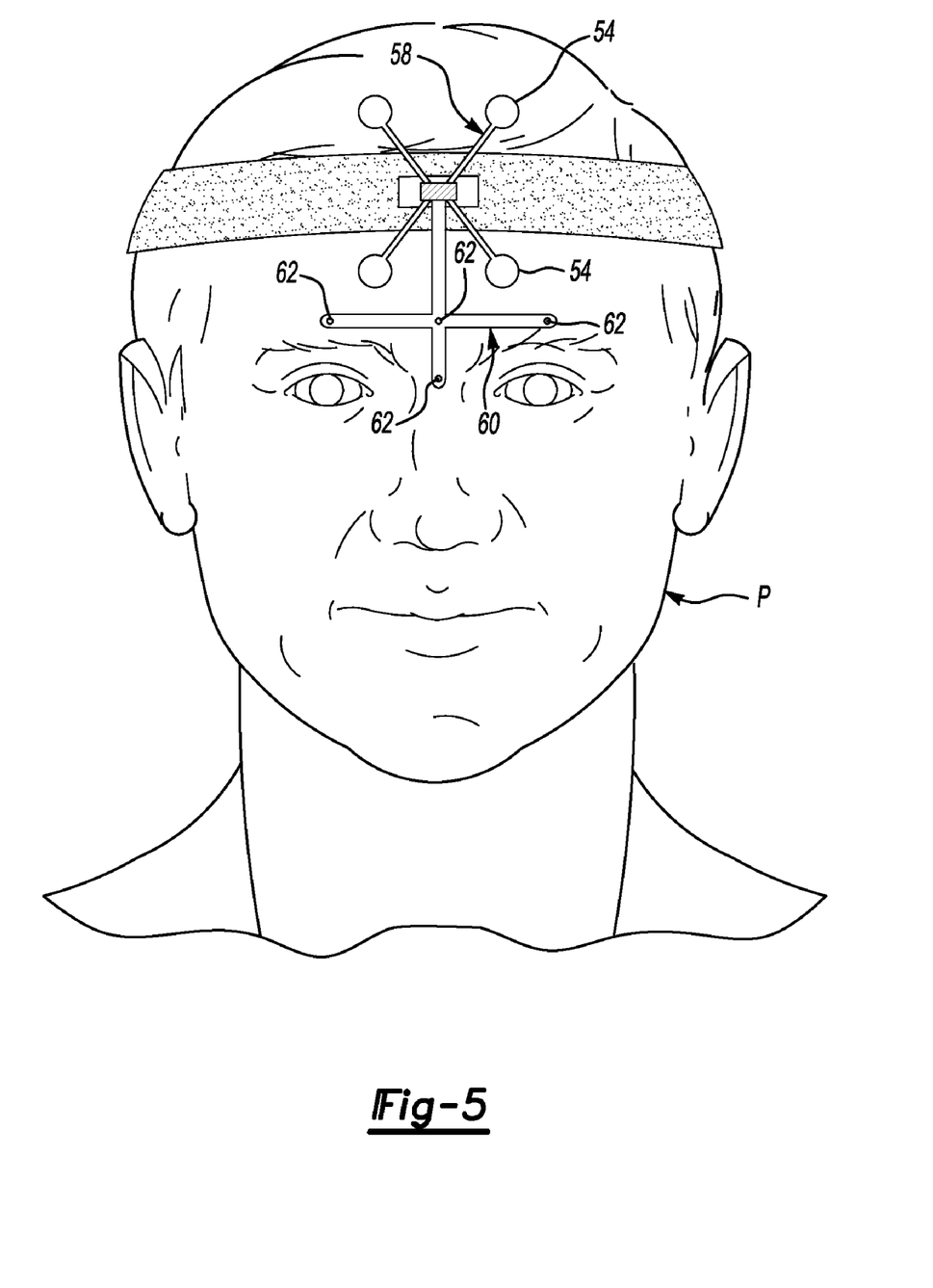
FIG. 5 illustrates a patient tracker with a registration appendage.

A registration appendage 60 is removably secured to the patient tracker 58 in a known position and orientation relative to the patient tracker 58, as shown in FIGS. 1 and 5. The registration appendage 60 includes three or four (or more, but preferably at least three) radio-opaque markers 62 arranged in a predetermined geometric pattern.

The registration appendage 60 particularly is secured to the patient tracker 58 in situations where the locators 54 are outside the field of view of the CT scanner 10. In one example, the patient tracker 58 is secured to a forehead of the patient P, and the registration appendage 60 is located between the patient tracker 58 and a body of the patient P. That is, the registration appendage 60 points towards the body and feet of the patient P.

When the CT scanner 10 takes a scan (a full scan or an update scan) of the patient P, the radio-opaque markers 62 of the registration appendage 60 are within the field of view of the CT scanner 10 and thus appear in a three-dimensional CT image. This permits repeatable registration of the position and orientation of the three-dimensional CT image relative to previous three-dimensional CT images. As the position and orientation of the radio-opaque markers 62 relative to the locators 54 are known, the current position and orientation of the patient P relative to the CT scanner 10 and thus, relative to the patient tracker 58, can be determined.

Figure 6:
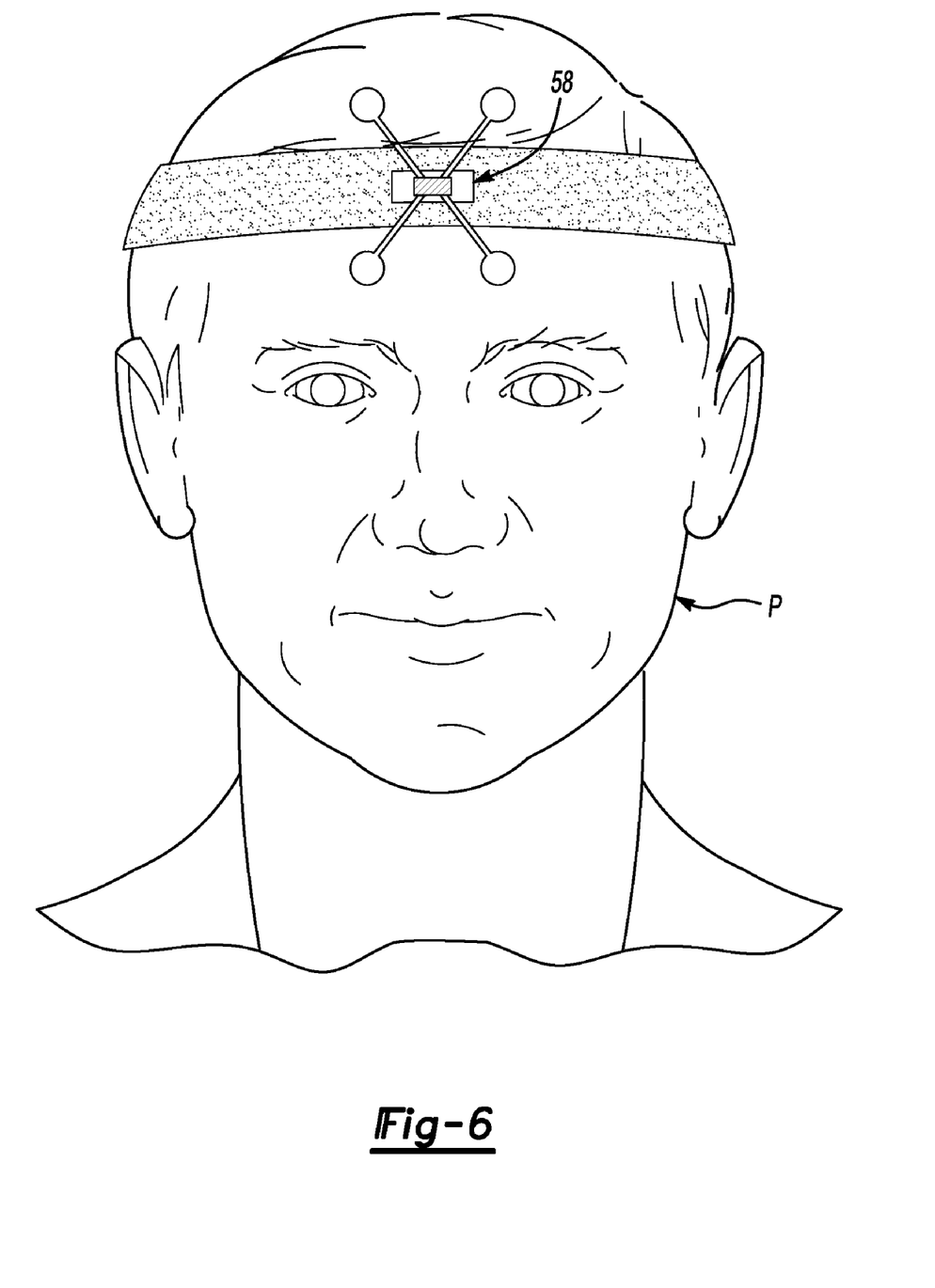
FIG. 6 illustrates the patient tracker without the registration appendage.

The registration appendage 60 can be removed from the patient tracker 58 after the scan is performed (as shown in FIG. 6), but the position of the patient P (and the three-dimensional CT image just generated by the CT scan) is still tracked relative to the patient tracker 58 by tracking the position and orientation of the patient tracker 58. The surgical navigation system 8 may require the surgeon to quickly verify the accuracy of the transformation between the radio-opaque markers 62 and the locators 54.

The tracking system 56 determines the position and orientation of the surgical instruments 52, the patient P and the CT scanner 10 based upon the locators 54 in any known manner, such that the position and orientation of the three-dimensional CT image of the patient P, the CT scanner 10 and the surgical instruments 52 and are all known relative to one another. The relative locations of the locators 54 and the three-dimensional CT image of the patient P are displayed on the display 36.

Figure 7:
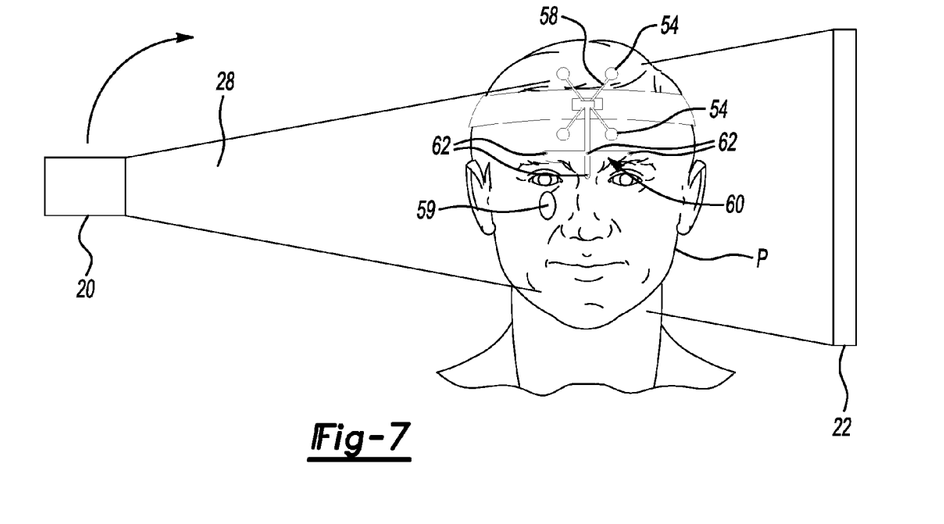
FIG. 7 illustrates a full field of view of a two-dimensional CT image.

In one example, as shown in FIG. 7, the locators 54 of the patient tracker 58 are in the path of the x-rays 28 during a full field of view CT scan. The CT scan can be a pre-operative CT scan or an intra-operative CT scan (full or partial). A volume of interest 59 of the patient P can be located using the pre-operative CT scan and the intra-operative CT scan.

Figure 8:
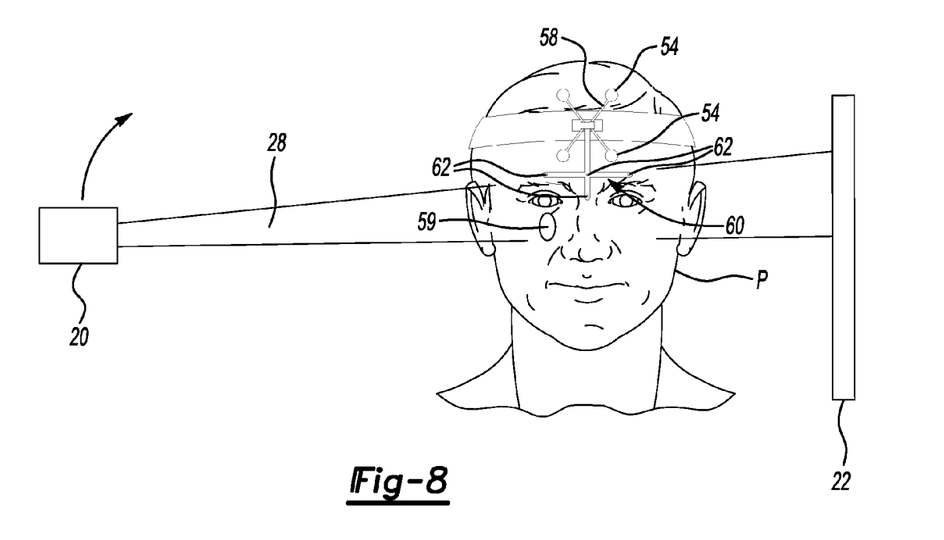
FIG. 8 illustrates a collimated field of view of a two-dimensional CT image that focuses on a volume of interest of the patient.

During surgery, the CT scanner 10 can take an intra-operative CT scan of the volume of interest 59 of the patient P so the surgeon can determine the current progress of the surgery (e.g., has a tumor been completely removed or a sinus cavity been completely repaired?). After locating the volume of interest 59, the CT scanner 10 collimates the x-ray source 20 (shown in FIG. 8) and takes a plurality of x-ray images at a plurality of angularly-spaced positions to perform a collimated intra-operative updated CT scan of the volume of interest 59. The computer 30 uses pre-operative data surrounding the volume of interest 59 in conjunction with the new information from the collimated intra-operative CT scan of the volume of interest 59 to create a fully updated three-dimensional CT image.

During a CT scan shown in FIG. 7, the locators 54 and the radio-opaque markers 62 are located in the field of view of the x-rays 28. When the collimated intra-operative CT scan is taken, the x-rays source 20 is collimated such that the locators 54 of the patient tracker 58 could be located outside the collimated field of view of the CT scanner 10 (that is, not in the path of the x-rays 28). When the CT scanner 10 performs the collimated CT scan, the radio-opaque markers 62 of the registration appendage 60 are located within the field of view of the CT scanner 10 and thus appear in the three-dimensional CT image. The radio-opaque markers 62 are viewable in both the previous CT images and the collimated CT image and can be used to register the collimated CT scan with the previous CT scans.

The foregoing description is only exemplary of the principles of the invention. Many modifications and variations are possible in light of the above teachings. It is, therefore, to be understood that within the scope of the appended claims, the invention may be practiced otherwise than using the example embodiments which have been specifically described. For that reason the following claims should be studied to determine the true scope and content of this invention.

What is claimed is:

1. A surgical navigation system comprising:
a CT scanner that performs a CT scan to generate a three dimensional CT image;
a patient tracker positioned on a patient including a plurality of locators in a fixed orientation, wherein the patient tracker is attached to a headband; and
an appendage removably secured to the patient tracker, wherein the appendage includes a plurality of markers in a fixed orientation that are viewable in the three dimensional CT image, and the plurality of markers are located over a face of the patient.

2. The surgical navigation system as recited in claim 1 further including a tracking system that tracks the plurality of locators.

3. The surgical navigation system as recited in claim 2 wherein the tracking system tracks the locators with one of an RF signal, an electromagnetic signal and an optical signal.

4. The surgical navigation system as recited in claim 1 further including a surgical instrument having at least one locator.

5. The surgical navigation system as recited in claim 1 wherein a locator is fixed to the CT scanner.

6. The surgical navigation system as recited in claim 1 wherein the plurality of markers are radio-opaque.

7. The surgical navigation system as recited in claim 1 wherein the CT scanner includes an x-ray source to generate x-rays and an x-ray detector mounted opposite the x-ray source.

8. The surgical navigation system as recited in claim 7 wherein the x-ray source is a cone-beam x-ray source.

9. The surgical navigation system as recited in claim 7 further including a gantry including a cross-bar section, a first arm and a second arm that each extend substantially perpendicularly to the cross-bar section, wherein the x-ray source is housed in the first arm and the x-ray detector is housed in the second arm.

10. The surgical navigation system as recited in claim 1 further including a display that display the three dimensional CT image.

11. The surgical navigation system as recited in claim 1 wherein the plurality of locators are in a first field of view of the CT scanner when the CT scanner takes a first CT scan and the plurality of locators are not in a second field of view of the CT scanner when the CT scanner takes a second CT scan.

12. The surgical navigation system as recited in claim 11 wherein the plurality of markers are in the first field of view and the second field of view of the CT scanner when the CT scanner takes the first CT scan and the second CT scan, respectively, and the plurality of markers are used to register a first three dimensional CT image of the first CT scan with a second three dimensional CT image of the second CT scan.

13. The surgical navigation system as recited in claim 11 wherein the first field of view is a full field of view and the second field of view is a collimated field of view.

14. The surgical navigation system as recited in claim 1 wherein the patient tracker is positioned on a head of the patient.

15. The surgical navigation system as recited in claim 1 wherein the appendage is located over a head of the patient.

16. The surgical navigation system as recited in claim 1 wherein the appendage is t-shaped.

17. The surgical navigation system as recited in claim 1 wherein the appendage is in a plane substantially parallel to a plane defined by the body of the patient.

18. The surgical navigation system as recited in claim 1 wherein the appendage is located between the patient tracker and feet of the patient.

19. The surgical navigation system as recited in claim 1 wherein the plurality of locators are located near an upper part of a head of the patient and the plurality of markers are located near a lower part of the head of the patient.

20. The surgical navigation system as recited in claim 1 wherein the plurality of markers are located between the patient tracker and a nose of the patient.

21. The surgical navigation system as recited in claim 1 wherein the appendage is t-shaped and includes a first arm and a second arm that is substantially perpendicular to the first arm, wherein the first arm is located between eyes of the patient and the second arm is located above the eyes of the patient such that the second arm is between the eyes of the patient and the patient tracker.

22. The surgical navigation system as recited in claim 1 wherein the plurality of locators are located in a single plane, and the plurality of markers are located in another single plane.

23. The surgical navigation system as recited in claim 1 wherein the appendage and the plurality of markers are located between the patient tracker and a body of the patient.

24. The surgical navigation system as recited in claim 1 wherein a majority of the appendage is located proximate to a nose of the patient and distal from a top of a head of the patient.

25. The surgical navigation system as recited in claim 1 wherein the patient tracker is substantially x-shaped.

26. The surgical navigation system as recited in claim 1 wherein the appendage extends towards a center of the three-dimensional CT image.

27. A method of tracking a patient, the method comprising the steps of:
   positioning a patient tracker including a plurality of locators on a patient, wherein the patient tracker is attached to a headband;
   removably attaching an appendage including a plurality of markers to the patient tracker, wherein the plurality of markers and the plurality of locators each have a fixed orientation; and
   performing a CT scan to generate a three dimensional CT image, wherein the plurality of markers are visible in the three dimensional CT image, and the plurality of markers are located over a face of the patient.

28. The method as recited in claim 27 further including the steps of locating a volume of interest in the patient and collimating an x-ray source to take a collimated CT scan of the volume of interest, wherein the plurality of markers on the appendage are visible in a collimated three dimensional CT image.

29. The method as recited in claim 27 further including the steps of tracking the plurality of locators of the patient tracker.

30. The method as recited in claim 27 further including the steps of performing a first CT scan and a second CT scan, wherein the plurality of locators are in a first field of view of the CT scanner when the CT scanner takes the first CT scan and the plurality of locators are not in a second field of view of the CT scanner when the CT scanner takes the second CT scan.

31. The method as recited in claim 30 further including the steps of generating a first CT image using the first CT scan, generating a second CT image using the second CT scan, and registering the first CT image to the second CT image using the plurality of markers.

32. The method as recited in claim 27 wherein the step of positioning the patient tracker includes positioning the patient tracker on a head of the patient.

33. The method as recited in claim 27 wherein the step of removably attaching the appendage includes attaching the appendage over a head of the patient.

34. The method as recited in claim 27 wherein the appendage is t-shaped.

35. The method as recited in claim 27 wherein the appendage is in a plane substantially parallel to a plane defined by the body of the patient.

36. The method as recited in claim 27 wherein the appendage is located between the patient tracker and feet of the patient.

37. The method as recited in claim 27 wherein the plurality of locators are located near an upper part of a head of the patient and the plurality of markers are located near a lower part of the head of the patient.

38. The method as recited in claim 27 wherein the plurality of markers are located between the patient tracker and a nose of the patient.

39. The method as recited in claim 27 wherein the appendage is t-shaped and includes a first arm and a second arm that is substantially perpendicular to the first arm, wherein the first arm is located between eyes of the patient and the second arm is located above the eyes of the patient such that the second arm is between the eyes of the patient and the patient tracker.

40. The method as recited in claim 27 wherein the plurality of locators are located in a single plane, and the plurality of markers are located in another single plane.

41. The method as recited in claim 27 wherein the appendage and the plurality of markers are located between the patient tracker and a body of the patient.

42. The method as recited in claim 27 wherein a majority of the appendage is located proximate to a nose of the patient and distal from a top of a head of the patient.

43. The method as recited in claim 27 wherein the patient tracker is substantially x-shaped.

44. The method as recited in claim 27 wherein the appendage extends towards a center of the three-dimensional CT image.

45. A surgical navigation system comprising:
- a CT scanner that performs a CT scan to generate a three dimensional CT image;
- a patient tracker positioned on a patient including a headband and a plurality of locators in a fixed orientation; and
- an appendage removably secured to the patient tracker, wherein the appendage includes a plurality of markers in a fixed orientation that are viewable in the three dimensional CT image, the plurality of markers are located over a face of the patient and the appendage is located between the patient tracker and feet of the patient.

46. The surgical navigation system as recited in claim 45 wherein the plurality of locators are located in a single plane, and the plurality of markers are located in another single plane.

* * * * *